(12) United States Patent
Hester et al.

(10) Patent No.: US 8,579,910 B2
(45) Date of Patent: Nov. 12, 2013

(54) INSERTION BLADE ASSEMBLY AND METHOD OF USE

(75) Inventors: Douglas Hester, Raynham, MA (US); Paul S. Maguire, Hope Valley, RI (US)

(73) Assignee: DePuy Synthes Products, LLC, Raynham, MA (US)

( * ) Notice: Subject to any disclaimer, the term of this patent is extended or adjusted under 35 U.S.C. 154(b) by 1156 days.

(21) Appl. No.: 11/750,470

(22) Filed: May 18, 2007

(65) Prior Publication Data

US 2008/0287957 A1 Nov. 20, 2008

(51) Int. Cl.
*A61B 17/88* (2006.01)
*A61F 2/46* (2006.01)

(52) U.S. Cl.
USPC ........................................................... 606/99

(58) Field of Classification Search
USPC .......................... 606/99, 100, 86 A, 86 B, 90
See application file for complete search history.

(56) References Cited

U.S. PATENT DOCUMENTS

| | | |
|---|---|---|
| 3,141,583 A | 7/1964 | Williams et al. |
| 3,752,161 A | 8/1973 | Bent |
| 3,835,860 A | 9/1974 | Garretson |
| 4,367,746 A | 1/1983 | Derechinsky |
| 4,512,345 A | 4/1985 | Green |
| 4,759,766 A | 7/1988 | Buettner-Janz et al. |
| 5,122,130 A | 6/1992 | Keller |
| 5,236,460 A | 8/1993 | Barber |
| 5,258,031 A | 11/1993 | Salib et al. |
| 5,300,081 A | 4/1994 | Young et al. |
| 5,314,477 A | 5/1994 | Marnay |
| 5,360,430 A | 11/1994 | Lin |
| 5,370,697 A | 12/1994 | Baumgartner |
| 5,425,773 A | 6/1995 | Boyd et al. |
| 5,431,654 A | 7/1995 | Nic |
| 5,431,658 A | 7/1995 | Moskovich |
| 5,458,641 A | 10/1995 | Ramirez Jimenez |

(Continued)

FOREIGN PATENT DOCUMENTS

| | | | |
|---|---|---|---|
| EP | 0535973 A1 | 4/1993 | |
| EP | 0630615 A1 | 12/1994 | |

(Continued)

OTHER PUBLICATIONS

Krag, M.H. et al. "An Internal Fixator for Posterior Application to Short Segments of the Thoracic, Lumbar, or Lumbosacral Spine", Clinical Orthopaedics and Related Research, 203: 75-98 (Feb. 1986).

*Primary Examiner* — Michael T Schaper

(74) *Attorney, Agent, or Firm* — Nutter McClennen & Fish LLP

(57) ABSTRACT

A spinal implant insertion device is hereby provided. The device includes an insertion blade assembly having a set of opposed insertion blades wherein the assembly is adapted to slide from a retracted position to an extended position relative to an elongate shaft. In the extended position, a blades are adapted to be positioned above and below a portion of a spinal implant so as to shield the portion of the implant during delivery to an intervertebral space. The insertion blades assembly can also be modular so as to utilize a wide range of distinct insertion blades. Additionally, a method for delivering a spinal implant to an intervertebral space is herein provided. Like above, the method utilizes an insertion blade assembly adapted to slide along a shaft of a spinal implant insertion device.

8 Claims, 15 Drawing Sheets

(56) References Cited

U.S. PATENT DOCUMENTS

| | | |
|---|---|---|
| 5,505,732 A | 4/1996 | Michelson |
| 5,507,816 A | 4/1996 | Bullivant |
| 5,562,738 A | 10/1996 | Boyd et al. |
| 5,591,170 A | 1/1997 | Spievack et al. |
| 5,676,701 A | 10/1997 | Yuan et al. |
| 5,683,465 A | 11/1997 | Shinn et al. |
| 5,782,830 A | 7/1998 | Farris |
| 5,782,832 A | 7/1998 | Larsen et al. |
| 5,797,927 A | 8/1998 | Yoon |
| 5,851,207 A | 12/1998 | Cesarone |
| 5,873,886 A | 2/1999 | Larsen et al. |
| 5,895,428 A | 4/1999 | Berry |
| 5,899,941 A | 5/1999 | Nishijima et al. |
| 5,931,849 A | 8/1999 | Desvignes et al. |
| 5,938,678 A | 8/1999 | Zirps et al. |
| 5,989,291 A | 11/1999 | Ralph et al. |
| 6,019,792 A | 2/2000 | Cauthen |
| 6,063,121 A | 5/2000 | Xavier et al. |
| 6,066,174 A | 5/2000 | Farris |
| 6,099,550 A | 8/2000 | Yoon |
| 6,110,179 A | 8/2000 | Flivik et al. |
| 6,113,605 A | 9/2000 | Storer |
| 6,113,637 A | 9/2000 | Gill et al. |
| 6,146,421 A | 11/2000 | Gordon et al. |
| 6,159,215 A | 12/2000 | Urbahns et al. |
| 6,174,311 B1 | 1/2001 | Branch et al. |
| 6,179,874 B1 | 1/2001 | Cauthen |
| 6,228,118 B1 | 5/2001 | Gordon |
| 6,261,296 B1 | 7/2001 | Aebi et al. |
| 6,296,665 B1 | 10/2001 | Strnad et al. |
| 6,319,257 B1 | 11/2001 | Carignan et al. |
| 6,358,268 B1 | 3/2002 | Hunt et al. |
| 6,368,350 B1 | 4/2002 | Erickson et al. |
| 6,371,986 B1 | 4/2002 | Bagby |
| 6,375,682 B1 | 4/2002 | Fleischmann et al. |
| 6,395,034 B1 | 5/2002 | Suddaby |
| 6,416,551 B1 | 7/2002 | Keller |
| 6,439,439 B1 | 8/2002 | Rickard et al. |
| 6,440,142 B1 | 8/2002 | Ralph et al. |
| 6,440,168 B1 | 8/2002 | Cauthen |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,540,785 B1 | 4/2003 | Gill et al. |
| 6,562,074 B2 | 5/2003 | Gerbec et al. |
| 6,579,320 B1 | 6/2003 | Gauchet et al. |
| 6,599,294 B2 | 7/2003 | Fuss et al. |
| 6,599,295 B1 | 7/2003 | Tornier et al. |
| 6,616,671 B2 | 9/2003 | Landry et al. |
| 6,648,891 B2 | 11/2003 | Kim |
| 6,652,533 B2 | 11/2003 | O'Neil |
| 6,652,534 B2 | 11/2003 | Zucherman et al. |
| 6,660,006 B2 * | 12/2003 | Markworth et al. ........ 606/86 A |
| 6,663,637 B2 | 12/2003 | Dixon et al. |
| 6,692,501 B2 | 2/2004 | Michelson |
| 6,712,818 B1 | 3/2004 | Michelson |
| 6,712,825 B2 | 3/2004 | Aebi et al. |
| 6,740,087 B2 | 5/2004 | Knox |
| 6,755,841 B2 | 6/2004 | Fraser et al. |
| 6,814,737 B2 | 11/2004 | Cauthen |
| 6,896,680 B2 | 5/2005 | Michelson |
| 6,986,772 B2 | 1/2006 | Michelson |
| 7,014,617 B2 | 3/2006 | Grinberg |
| 7,081,118 B2 | 7/2006 | Weber et al. |
| 7,118,580 B1 | 10/2006 | Beyersdorff et al. |
| 7,204,851 B2 | 4/2007 | Trieu et al. |
| 7,314,468 B2 | 1/2008 | Michelson |
| 2001/0016741 A1 * | 8/2001 | Burkus et al. ................ 606/57 |
| 2001/0029377 A1 | 10/2001 | Aebi et al. |
| 2001/0031969 A1 | 10/2001 | Aebi et al. |
| 2002/0011687 A1 | 1/2002 | Mischo |
| 2002/0035400 A1 | 3/2002 | Bryan et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0116009 A1 | 8/2002 | Fraser et al. |
| 2002/0128659 A1 | 9/2002 | Michelson |
| 2002/0128714 A1 | 9/2002 | Manasas et al. |
| 2002/0128715 A1 | 9/2002 | Bryan et al. |
| 2002/0161366 A1 | 10/2002 | Robie et al. |
| 2002/0161375 A1 | 10/2002 | Ralph et al. |
| 2002/0173813 A1 | 11/2002 | Peterson et al. |
| 2003/0033016 A1 | 2/2003 | Dees |
| 2003/0040802 A1 | 2/2003 | Errico et al. |
| 2003/0055434 A1 | 3/2003 | O'Neil |
| 2003/0060687 A1 | 3/2003 | Kleeman et al. |
| 2003/0065395 A1 | 4/2003 | Ralph et al. |
| 2003/0069586 A1 | 4/2003 | Errico et al. |
| 2003/0069643 A1 | 4/2003 | Ralph et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0074076 A1 | 4/2003 | Ferree et al. |
| 2003/0078664 A1 | 4/2003 | Ralph et al. |
| 2003/0078665 A1 | 4/2003 | Ralph et al. |
| 2003/0078666 A1 | 4/2003 | Ralph et al. |
| 2003/0083747 A1 | 5/2003 | Winterbottom et al. |
| 2003/0135220 A1 | 7/2003 | Cauthen |
| 2003/0135277 A1 | 7/2003 | Bryan et al. |
| 2003/0135278 A1 | 7/2003 | Eckman |
| 2003/0135375 A1 | 7/2003 | Bloomstein |
| 2003/0149438 A1 | 8/2003 | Nichols et al. |
| 2003/0149482 A1 | 8/2003 | Michelson |
| 2003/0171813 A1 | 9/2003 | Kiester |
| 2003/0187454 A1 | 10/2003 | Gill et al. |
| 2003/0199872 A1 | 10/2003 | Markworth et al. |
| 2003/0216744 A1 | 11/2003 | Longhini et al. |
| 2004/0002758 A1 | 1/2004 | Landry et al. |
| 2004/0030387 A1 | 2/2004 | Landry et al. |
| 2004/0039397 A1 | 2/2004 | Weber et al. |
| 2004/0082958 A1 | 4/2004 | Michelson |
| 2004/0167534 A1 | 8/2004 | Errico et al. |
| 2004/0167537 A1 | 8/2004 | Errico et al. |
| 2004/0176773 A1 | 9/2004 | Zubok et al. |
| 2004/0215198 A1 | 10/2004 | Marnay et al. |
| 2004/0225295 A1 | 11/2004 | Zubok et al. |
| 2004/0267275 A1 * | 12/2004 | Cournoyer et al. ............. 606/99 |
| 2005/0015094 A1 | 1/2005 | Keller |
| 2005/0015095 A1 | 1/2005 | Keller |
| 2005/0021040 A1 | 1/2005 | Bertagnoli |
| 2005/0021042 A1 | 1/2005 | Marnay et al. |
| 2005/0027300 A1 | 2/2005 | Hawkins et al. |
| 2005/0033305 A1 * | 2/2005 | Schultz ........................... 606/99 |
| 2005/0033428 A1 | 2/2005 | Keller |
| 2005/0038511 A1 | 2/2005 | Martz et al. |
| 2005/0043740 A1 | 2/2005 | Haid et al. |
| 2005/0043741 A1 | 2/2005 | Michelson |
| 2005/0043800 A1 | 2/2005 | Paul et al. |
| 2005/0055029 A1 | 3/2005 | Marik et al. |
| 2005/0055031 A1 | 3/2005 | Lim |
| 2005/0055098 A1 | 3/2005 | Zdeblick et al. |
| 2005/0071013 A1 | 3/2005 | Zubok et al. |
| 2005/0119665 A1 | 6/2005 | Keller |
| 2005/0143747 A1 * | 6/2005 | Zubok et al. .................... 606/90 |
| 2005/0143749 A1 | 6/2005 | Zalenski et al. |
| 2005/0165408 A1 | 7/2005 | Puno et al. |
| 2005/0177173 A1 | 8/2005 | Aebi et al. |
| 2006/0004377 A1 | 1/2006 | Keller |
| 2006/0025777 A1 | 2/2006 | Weber |
| 2006/0030857 A1 | 2/2006 | de Villiers et al. |
| 2006/0030862 A1 | 2/2006 | De Villiers et al. |

(56) References Cited

U.S. PATENT DOCUMENTS

| | | |
|---|---|---|
| 2006/0036261 A1 | 2/2006 | McDonnell |
| 2006/0064107 A1 | 3/2006 | Bertagnoli et al. |
| 2006/0089656 A1 | 4/2006 | Allard et al. |
| 2006/0167461 A1 | 7/2006 | Hawkins et al. |
| 2006/0195097 A1 | 8/2006 | Evans et al. |
| 2006/0241641 A1 | 10/2006 | Albans et al. |
| 2007/0016220 A1 | 1/2007 | Michelson |
| 2007/0116221 A1 | 5/2007 | Kim |
| 2007/0123903 A1 | 5/2007 | Raymond et al. |
| 2007/0123904 A1 | 5/2007 | Stad et al. |
| 2007/0123907 A1 | 5/2007 | Weber |
| 2007/0191857 A1 | 8/2007 | Allard et al. |
| 2007/0198025 A1 | 8/2007 | Trieu et al. |
| 2007/0213739 A1 | 9/2007 | Michelson |
| 2007/0233143 A1 | 10/2007 | Josse et al. |
| 2007/0233153 A1 | 10/2007 | Shipp et al. |
| 2008/0065095 A1 | 3/2008 | Ralph et al. |
| 2008/0269764 A1 * | 10/2008 | Blain et al. .............. 606/99 |

FOREIGN PATENT DOCUMENTS

| | | |
|---|---|---|
| FR | 2636227 A1 | 3/1990 |
| FR | 2717068 A1 | 9/1995 |
| WO | 9622747 A1 | 8/1996 |
| WO | 9738634 A1 | 10/1997 |
| WO | 03077808 A2 | 9/2003 |
| WO | 2004041131 A2 | 5/2004 |
| WO | 2004089224 A2 | 10/2004 |
| WO | 2006033067 A2 | 3/2006 |

* cited by examiner

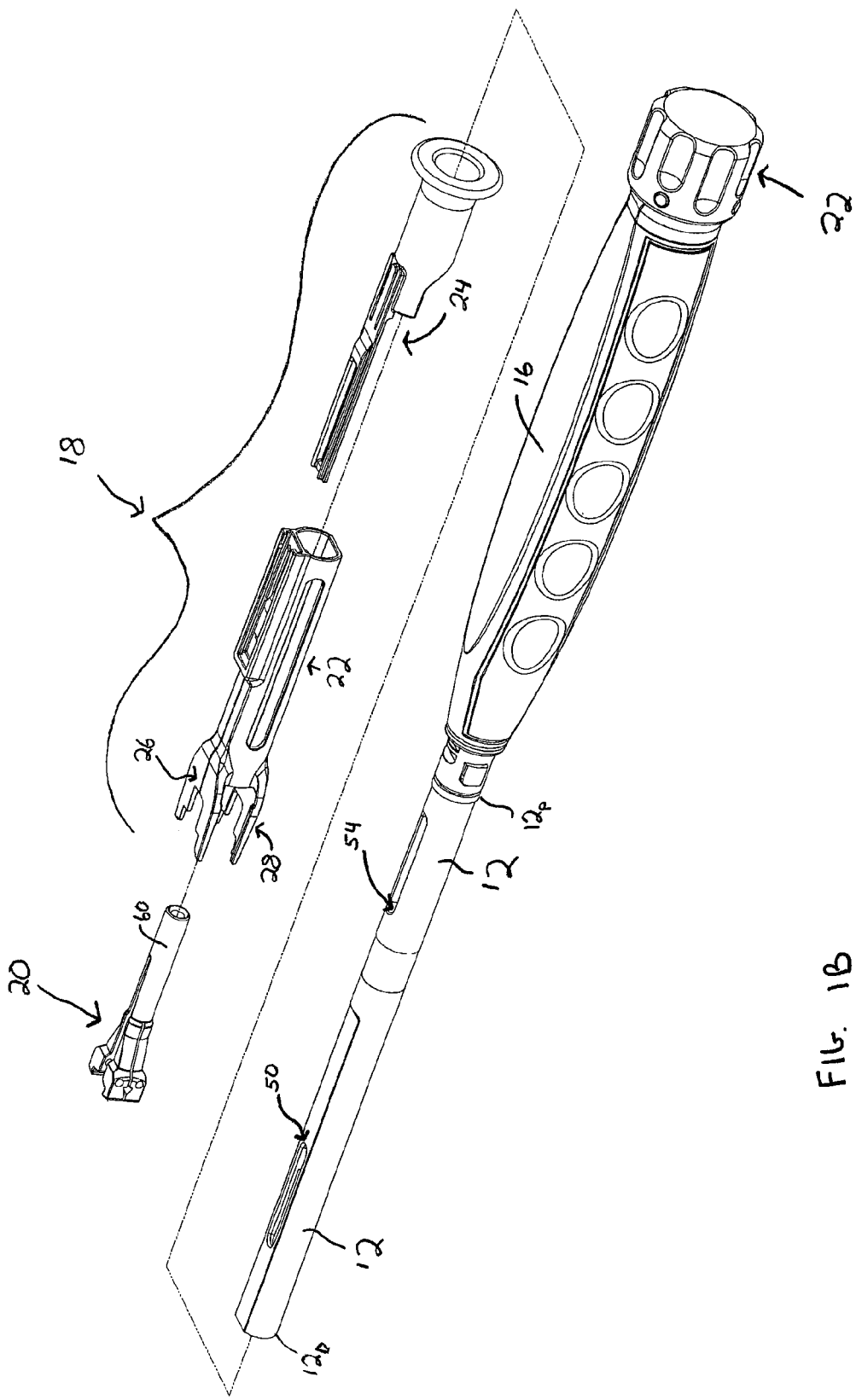

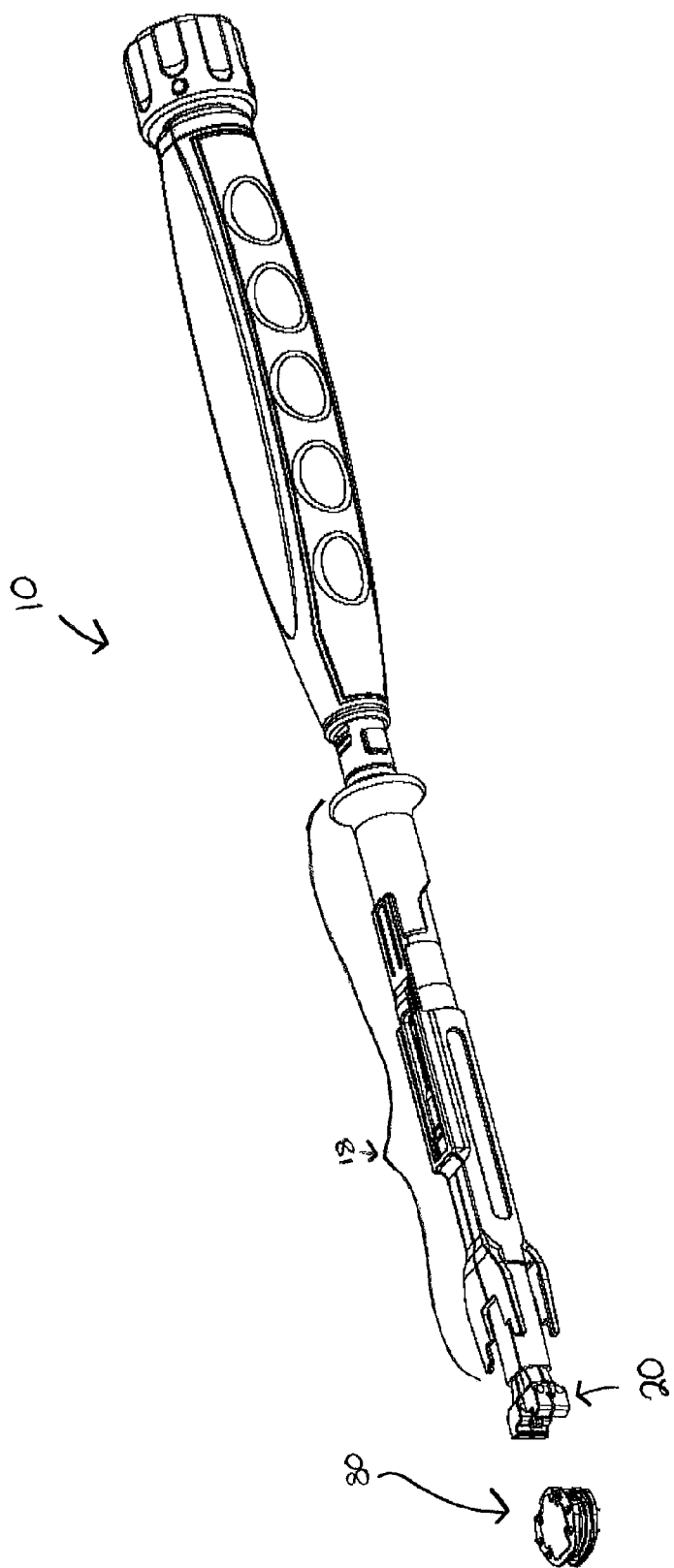

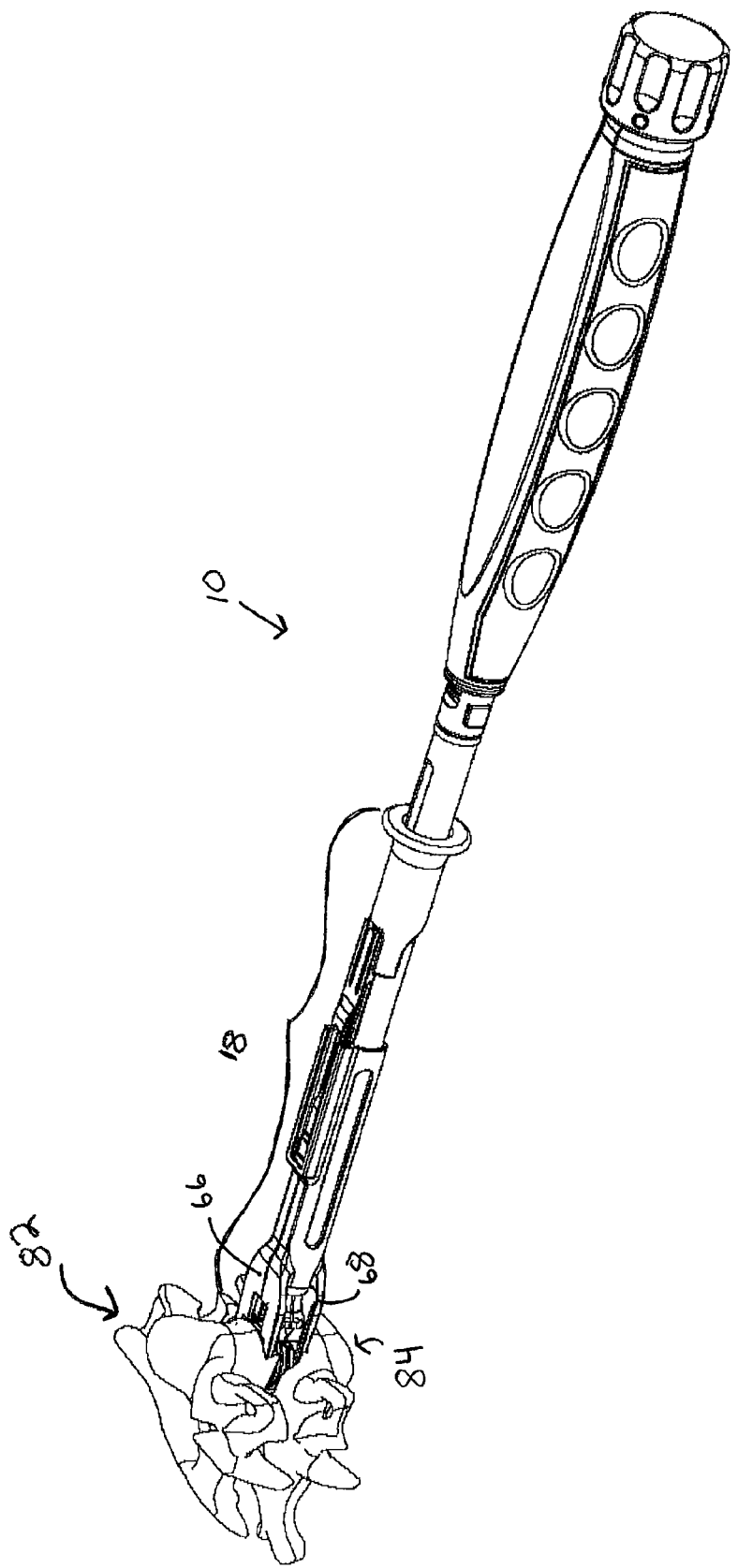

INSERTION BLADE ASSEMBLY AND METHOD OF USE

FIELD OF USE

The invention relates to devices and methods for positioning a spinal implant within an anatomical location, in particular, for inserting an artificial disc within an intervertebral space.

BACKGROUND

Spinal surgery involves many challenges as the long-term health and mobility of the patient often depends on the surgeon's technique and precision. One type of spinal surgery involves the removal of the natural disc tissue that is located between adjacent vertebral bodies. Procedures are known in which the natural, damaged disc tissue is replaced with an interbody cage or fusion device, or with an artificial disc prosthesis.

The insertion of a fusion device or an artificial disc prosthesis in the intervertebral space presents the surgeon with several challenges. For example, the adjacent vertebral bodies collapse upon each other once the natural disc tissue is removed. These bodies must be separated to an extent sufficient to enable the placement of the prosthesis. However, if the vertebral bodies are separated, or distracted, beyond a certain degree, further injury can occur. Also, the disc prosthesis must be precisely positioned between the adjacent vertebral bodies. Over-insertion or under-insertion of the prosthesis can lead to pain, postural problems, and/or limited mobility or freedom of movement.

As a further complication, some implants include a series of bone-engaging protrusions (e.g., teeth) extending from both the superior and inferior surfaces, which are intended to engage a corresponding vertebral endplate of adjacent vertebrae to enhance fixation of the implant. While assisting in securely positioning the implant, such protrusions can complicate delivery due to premature engagement during delivery as the protrusions typically engage the corresponding vertebral endplates before the implant has reached the desired location.

As such, there is a need for a device and method to facilitate the proper and convenient insertion of an implant between adjacent vertebral bodies while minimizing the risk of further injury to the patient.

SUMMARY

A device and method for positioning a spinal implant (such as an artificial disc) within an anatomical location is provided. More specifically, the device and method are adapted to shield portions of a superior and/or inferior surface of an implant from respective vertebral endplates of adjacent vertebrae as the implant is positioned within the intervertebral space. Once properly positioned, the device is adapted to securely hold the implant while allowing for engagement (or contact) of the vertebral endplates to the implant (for example, by sliding a shielding element out of and away from the intervertebral space). Following proper positioning and any necessary impaction, the implant can be released from the device, and the device removed from the treatment area. Various aspects of the device and method are summarized below.

In one aspect, a spinal implant insertion device is provided. The device includes an elongate shaft with a proximal end, a distal end, and a longitudinal axis extending therebetween. The device also includes an insertion blade assembly configured to slidably mate to an outer portion of the elongate shaft wherein a distal portion of the insertion blade assembly forms a set of opposed blades. The opposed blades include a first blade positioned above the longitudinal axis of the shaft and a second blade positioned below the longitudinal axis of the shaft. The set of opposed insertion blades can take a variety of configurations. For example, at least one of the first and second insertion blades can be substantially planar. Additionally, at least one of the first and second insertion blades can be substantially U-shaped, having a distal facing opening.

The insertion blade assembly is configured to slide between a retracted position and an extended position relative to the elongate shaft of the device. The insertion blade assembly can include an inner lumen having a locking mechanism configured to mate to complementary locking mechanism(s) on the outer portion of the elongate shaft to selectively lock the insertion blade assembly at a desired position (i.e., the extended or retracted position). In the retracted position, a distal end of each of the first and second insertion blades is configured to be positioned proximal to an implant held by a grasper element. In the extended position, the distal end of each of the first and second blades covers at least a portion of the implant held by the grasper element. As such, in the extended position, the blades are adapted to shield a portion of the implant from respective vertebral endplates of adjacent vertebra while the implant is positioned within an intervertebral space.

As mentioned above, the grasper element is adapted to grasp and hold a spinal implant. The grasper element is coupled to the distal end of the elongate shaft and adapted to move between a first, open position and a second, closed position such that the grasper element can securely grasp the implant when in the closed position. Additionally, the device can include an actuator coupled to the handle and in communication with the grasper element such that the actuator can move the grasper element between the open and closed positions in response to an external force (e.g., a user supplied force). Various such actuators can be utilized, for example, a rotation knob capable of opening and closing the grasper element in response to a rotational force.

In another aspect, an insertion blade assembly adapted to slide along an elongate shaft of a spinal insertion device is provided. The insertion blade assembly includes an assembly shaft having a distal end, a proximal end, and an inner lumen with a longitudinal axis extending therebetween. The inner lumen of the insertion blade assembly is configured to receive an outer portion of the spinal implant insertion device such that the assembly shaft is able to slide between a retracted position and an extended position relative to the elongate shaft of the device. The insertion blade assembly includes a set of opposed insertion blades extending from the distal end of the assembly shaft. The set of blades includes a first blade positioned above the longitudinal axis of the elongate shaft, and a second, blade positioned below the longitudinal axis of the central shaft. Optionally, the set of insertion blades can be releasably engaged to the assembly shaft thereby allowing for distinct sets of blades (e.g., different shape, size, configuration, etc.) to be engaged to the same assembly shaft. Such a modular device allows for added versatility and efficiency in delivering implants of various shapes and sizes to various anatomical locations.

In yet another aspect, a method for positioning a spinal implant within an anatomical location is provided. The method includes grasping a spinal implant with a grasper element of a spinal implant insertion device. Once the implant is held by the grasper element, the method includes sliding a pair of opposed insertion blades along an elongate shaft of the insertion device from a retracted position to an extended position such that in the extended position a top blade is positioned above a portion of the superior surface of the spinal implant and a bottom blade is positioned below a corresponding portion of the inferior surface of the spinal implant. Next, the method includes positioning the implant within the desired anatomical location (e.g., an intervertebral space), and sliding the blades from the extended position to the retracted position. Finally, the method includes releasing the spinal implant from the device. Additionally, the method can include locking the opposed insertion blades to the elongate shaft of the spinal insertion device when the blades are in a desired position (i.e., the extended position or the retracted position).

These and other aspects of the device and method provided herein are discussed in detail below.

BRIEF DESCRIPTION OF THE DRAWINGS

The invention will be more fully understood from the following detailed description taken in conjunction with the accompanying drawings, in which:

FIG. 1B is a partially exploded view of the device of FIG. 1A;

FIG. 6A is a perspective view of the device of FIG. 1 approaching a spinal implant;

FIG. 6D is a view of the device of FIG. 1 wherein the implant is positioned within a desired anatomical location;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
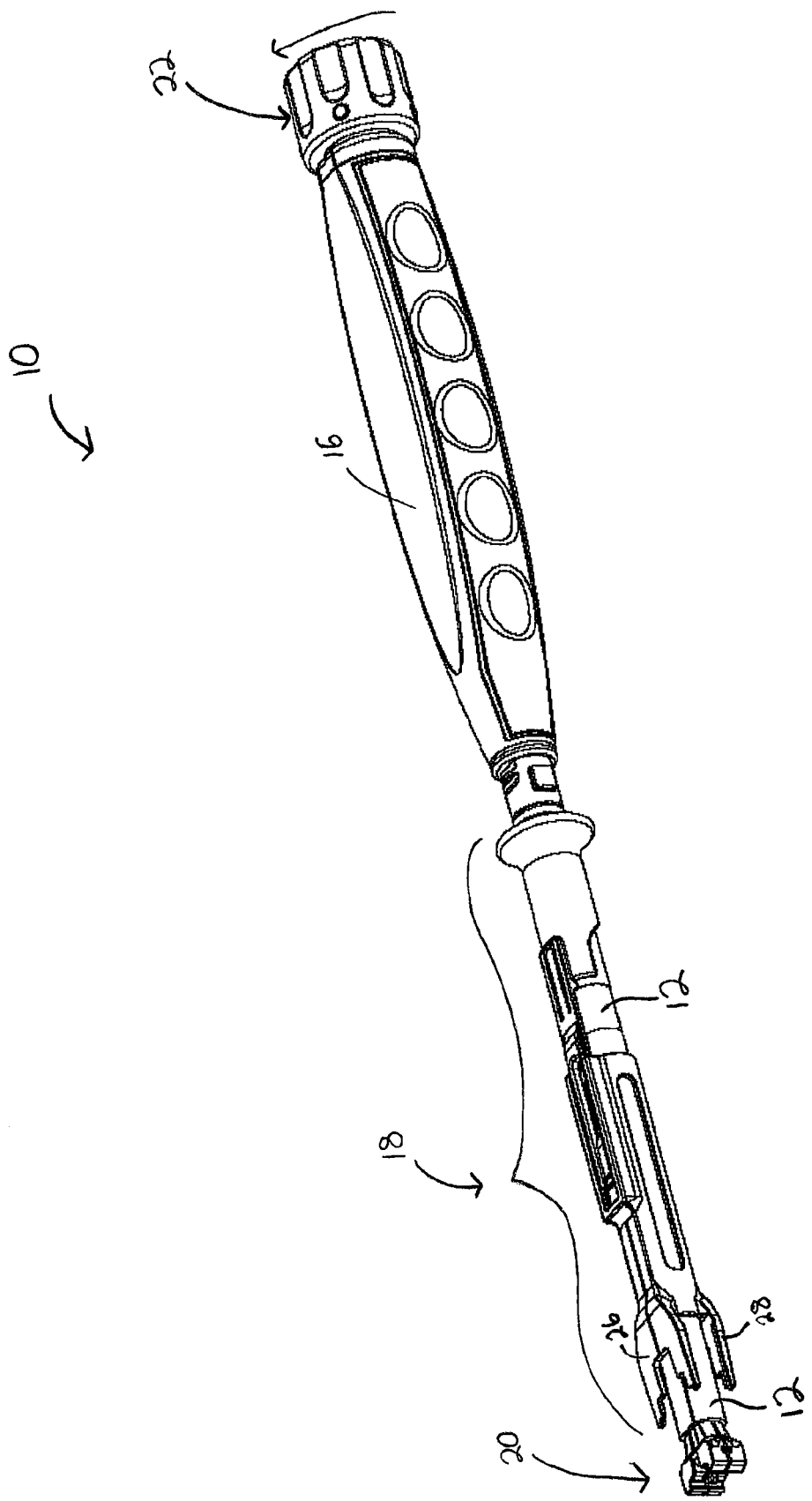
FIG. 1A is a perspective view of an exemplary embodiment of a spinal implant insertion device.

FIGS. 1A-1B provide an exemplary embodiment of a spinal implant insertion device 10. As shown, the device 10 includes an elongate shaft 12 extending from a handle 16 portion. More specifically, the elongate shaft 12 includes a proximal end ($12_P$) extending from a distal portion of the handle 16, and the shaft 12 terminates in a distal end ($12_D$) having an opening (see element 62 in FIG. 4) in communication with an inner lumen (not shown) extending within the shaft 12 between its proximal ($12_P$) and distal ends ($12_D$). The device 10 further includes an insertion blade assembly 18 slidably engaged to the elongate shaft 12. A distal portion of the insertion blade assembly 18 includes a set of opposed blades 26, 28 configured to be positioned on opposite sides of a longitudinal axis 11 (see FIG. 3A) of the shaft 12. As will be discussed, the insertion blade assembly 18 can slide from a retracted position (as shown, for example, in FIG. 1A) to an extended position (as shown, for example, in FIG. 6C). Generally speaking, while in the retracted position, the distal end of the blades 26, 28 are positioned proximal of an implant held by the device 10, and while in the extended position, at least a distal portion of the blades 26, 28 are positioned above and/or below at least a portion of a spinal implant held by the device 10 so as to shield the implant from respective vertebral endplates during positioning within an intervertebral space.

The device 10 further includes a grasper element 20 adapted to grasp and release the spinal implant. As shown in FIG. 1B, a proximal portion 60 of the grasper element 20 can be disposed within the distal opening of the shaft 12 so as to couple the grasper element 20 to the device 10. As will be discussed in detail below, the grasper element 20 can further be coupled to an actuator 22 (via a connector element discussed below) such that an external force (e.g., a rotational force) applied to the actuator 22 can force the grasper element 20 to open and close so as to grasp and/or release a spinal implant. These components, and others, will now be discussed in detail.

Figure 2A:
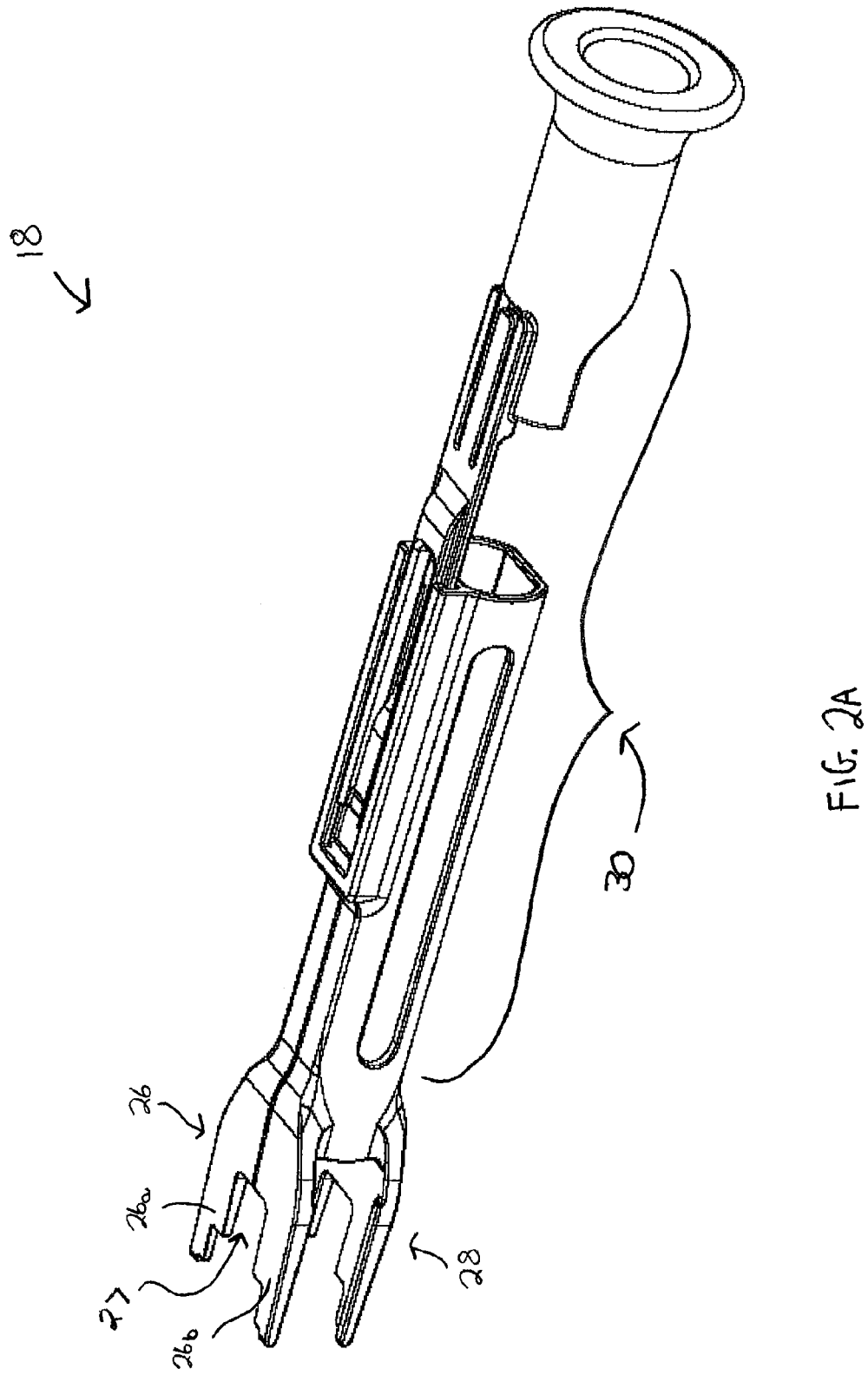
FIG. 2A is a perspective view of an exemplary embodiment of an insertion blade assembly.
Figure 2B:
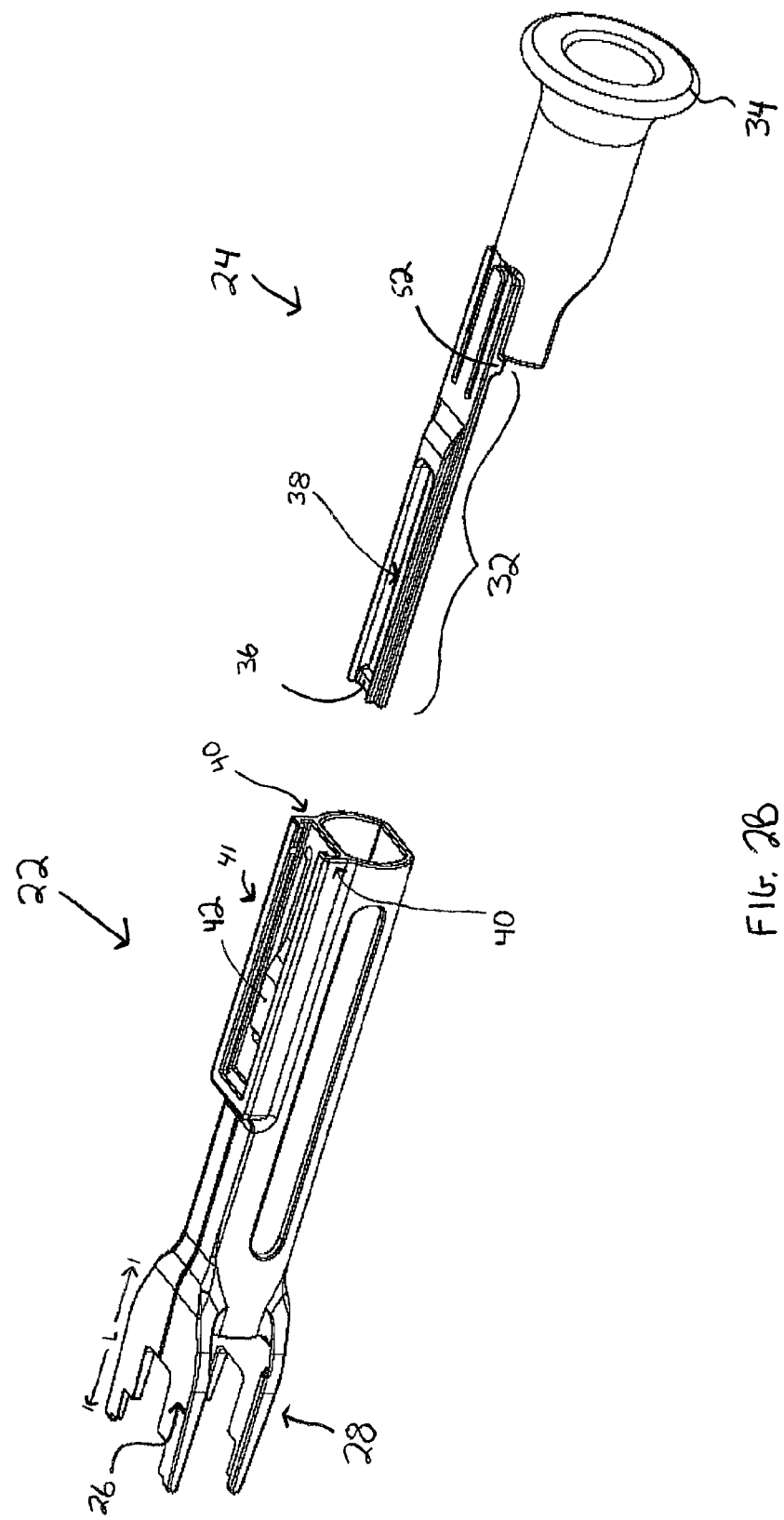
FIG. 2B is an exploded view of the insertion blade assembly of FIG. 2A.

FIGS. 2A and 2B provide an exemplary embodiment of the insertion blade assembly 18. As shown, the insertion blade assembly 18 generally includes an assembly shaft 30 which extends into a set of opposed insertion blades 26, 28. In an exemplary embodiment, the set of insertion blades includes a first insertion blade 26 positioned above a longitudinal axis 11 (substantially collinear with longitudinal axis of shaft 12) of the assembly shaft 30, and a second insertion blade 28 positioned below the longitudinal axis 11 of the assembly shaft 30. In one embodiment, the top blade 26 and the bottom blade 28 can be an equal distance above and below the longitudinal axis, respectively. In other embodiments, the top or bottom blade 26 can be positioned closer to or further from the longitudinal axis of the assembly shaft 30 as compared to the corresponding blade 28. As such, the blades 26, 28 can be positioned relative to one another in any manner as required by a given procedure.

Additionally, each blade 26, 28 of the insertion blade assembly 18 can have any of a wide range of possible configurations, sizes, dimensions, etc. In general, the blades 26, 28 can have any configuration capable of shielding a portion of a spinal implant from respective vertebral endplates as the implant is positioned within an intervertebral space. For example, at least one of the first and second insertion blades 26, 28 can be substantially planar. In another example (as shown in FIGS. 2A and 2B), at least one of the first and second insertion blades 26, 28 have a substantially "U-shaped" configuration wherein each plate 26, 28 includes a distal-facing opening 27. In such a configuration, at least one of the insertion blades 26 can include a first portion 26a adapted to shield a first set of protrusions positioned along one surface (e.g., a right surface) of a spinal implant, and a second portion 26b of the blade 26 can be adapted to shield a second set of protrusions positioned along an opposite surface (e.g., a left surface) of the spinal implant. As such, the blades 26, 28 can have any such configuration so as to correspond to any pattern of protrusions formed on an implant. Further, the blades 26, 28 can be configured to provide additional benefits. For example, the distal-facing opening 27 can provide for cost savings by using less material. Also, the opening 27 provides enhanced visibility to a user thereby allowing for better positioning of the implant within the intervertebral space.

As will be apparent to one skilled in the art, the first and second insertion blades 26, 28 can be substantially identical in size, shape, configuration, etc., or the blades 26, 28 can be distinct in one or all of these variables. Any such combination of insertion blades 26, 28 is within the spirit and scope of the present invention. Additionally, the blades 26, 28 can include a wide range of dimensions. For example, referring to FIG. 2B, a length ("L") of the insertion blade 26 can be in the range of about 16 mm to about 24 mm. Those skilled in the art will appreciate that such insertion blades 26, 28 of any dimensions are within the spirit and scope of the present invention.

The insertion blade assembly 18 can be a one-piece assembly, or the assembly 18 can be a modular design wherein various insertion blade portions can be releasably engaged to a single handle portion to form a complete insertion blade assembly 18. As shown in FIG. 2B, the insertion blade portion 22 can release from a handle portion 24. Such an embodiment allows for a wide range of insertion blades 26, 28 having different sizes, shapes, dimensions, configurations, etc. to be engaged to the handle portion 24 thereby providing a versatile device capable of being utilized with several implants and/or procedures. A wide range of mechanisms can be utilized to releasably mate the insertion blade portion 22 and the handle portion 24. For example, the exemplary embodiment of FIG. 2B provides a snap fitting between an extension 32 of the handle portion 24 and a corresponding snap-fitting 41 of the blade assembly portion 22. More specifically, the extension 32 includes a central opening 38 which terminates with a distal bar 36. In coupling the extension 32 to the corresponding snap fitting 41, the distal end of the extension 32 is inserted into a groove 40 configured to accept the extension 32. As the extension is slid in a distal direction, the distal bar 36 encounters a locking element 42. The locking element 42 includes a ramped proximal end, and the locking element 42 is biased in an upward position (i.e., locking mechanism 42 can move downward in response to a force). As the distal bar 36 slides up the ramped portion of the locking element 42, a downward pressure is exerted on the locking element 42 such that the locking element 42 moves downward to allow the bar 36 to pass over the locking element 42. Once the bar 36 is positioned distal of the locking element 42, the locking element 42 snaps back to the original biased upward configuration such that the locking element 42 is positioned in the central opening 38 of the extension 32. Due to the configuration of the distal end of the locking element 42, the distal bar 36 is prevented from passing back over the locking element 42. As such, the insertion blade portion 22 is now securely coupled to the handle portion 24 to form a complete insertion blade assembly 18 capable of being slidably mounted to the central shaft 12 of the spinal insertion device 10.

Figure 3A:
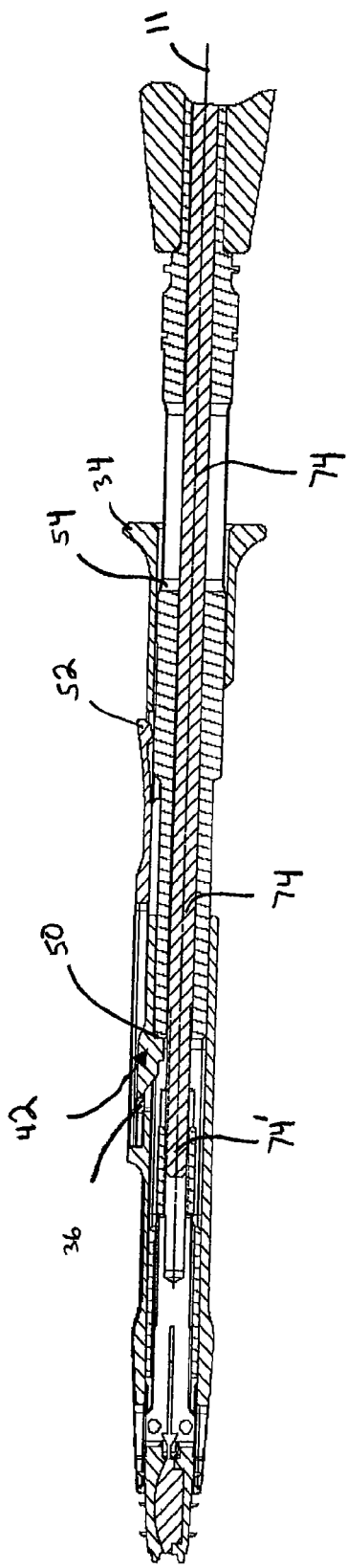
FIG. 3A is a cross-sectional view of the device of FIG. 1 showing the insertion blade assembly locked relative to the elongate shaft in an extended position.
Figure 3B:
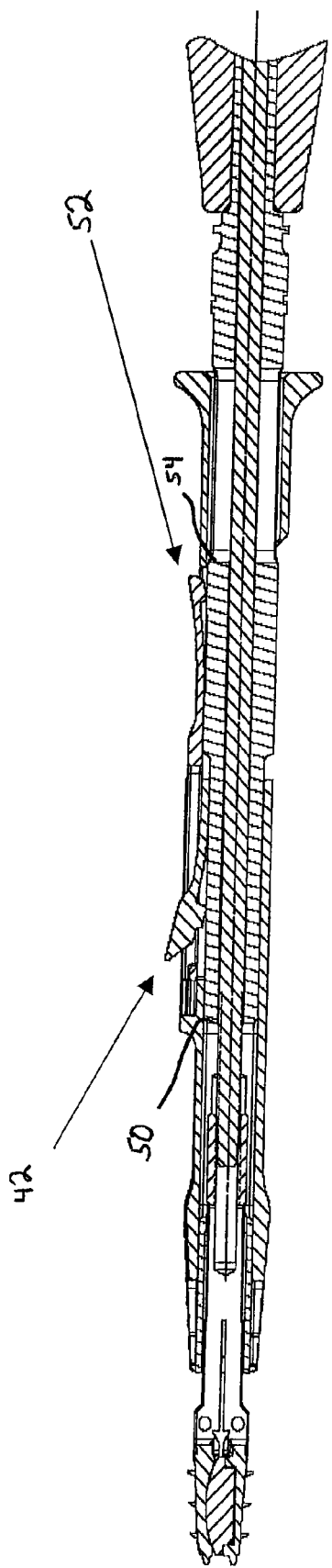
FIG. 3B is a cross-sectional view of the device of FIG. 1 showing the insertion blade assembly sliding from the extended to retracted position.
Figure 3C:
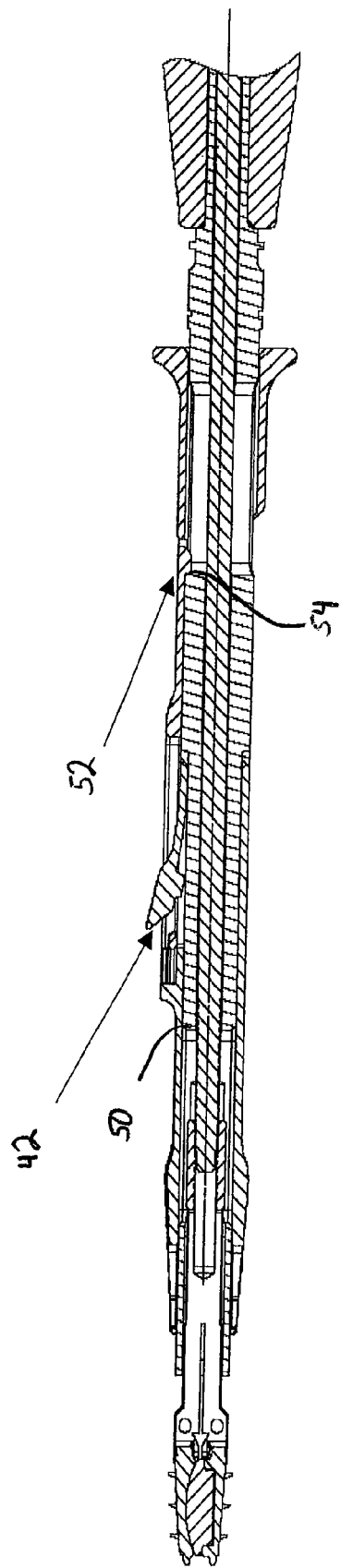
FIG. 3C is another cross-sectional view of the device of FIG. 1 showing the insertion blade assembly locked in the retracted position.
Figure 4:
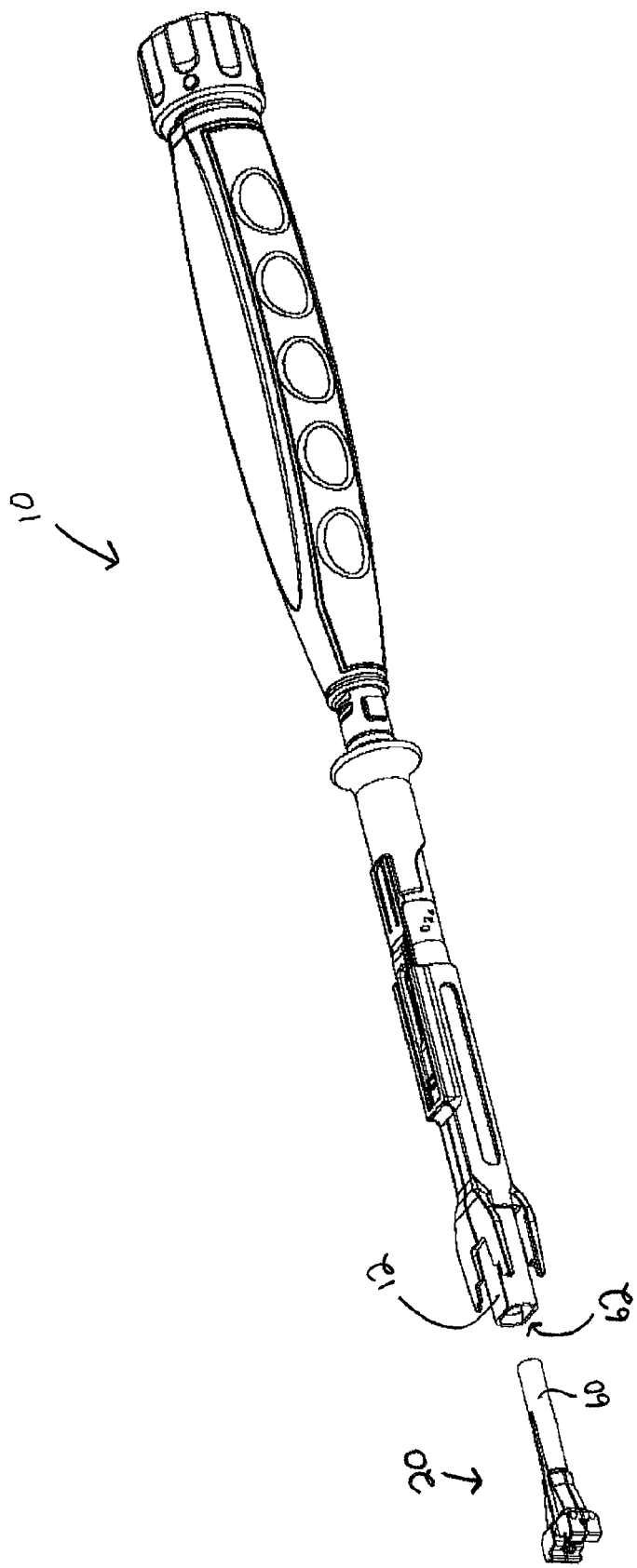
FIG. 4 is another partially exploded view of the device of FIG. 1.

In an exemplary embodiment, the device 10 can be adapted to include a locking mechanism capable of locking the insertion blade assembly 18 relative to the elongate shaft 12 of the device 10 at least one desired position (for example, at the extended position and/or the retracted position). Various such locking mechanisms are within the spirit and scope of the present invention. For example, as illustrated in FIGS. 3A-3C, a bottom portion of the locking element 42 (discussed immediately above) can be adapted to engage a first groove 50 (see FIG. 1B) incorporated into the elongate shaft 12. When the locking element 42 is engaged to the first groove 50, as shown in FIG. 3A, the assembly 18 is locked in an extended position relative to the shaft 12. As is also shown in FIG. 3A, the distal bar 36 (discussed above) is positioned immediately distal of a pointed distal portion of the locking element 42. In such an orientation, as a proximal force is applied to a terminal flange 34, the distal bar 36 can lift the locking element 42 to a necessary height so as to allow the locking element 42 to exit the groove 50 and slide in a proximal direction. As shown in FIG. 3B, as the assembly 18 is positioned between the extended and retracted positions, the locking element 42 is free to slide along the elongate shaft 12 due to the absence of any grooves in the shaft. Also, a second locking element 52 (also see FIG. 2B) is free to move in a proximal direction along the shaft. However, as shown in FIG. 3C, as the assembly 18 continues to move in a proximal direction towards the retracted position, the second locking mechanism 52 eventually engages a second groove 54 (also, see FIG. 1B) incorporated into the elongate shaft 12. When so engaged, the second locking mechanism 52 can prevent the assembly 18 from moving distally thereby locking the assembly 18 in the retracted position. In this embodiment, the locking mechanisms 42, 52 are adapted such that a minimal proximal or distal force applied to the terminal flange 34 can "unlock" the locking mechanism. As mentioned above, any such locking mechanism capable of securing the assembly at any desired location is within the spirit and scope of the present invention. Optionally, the device can be adapted to not utilize any type of locking mechanism but rather rely on the user to properly position and secure the insertion blade assembly 18.

Figure 5:
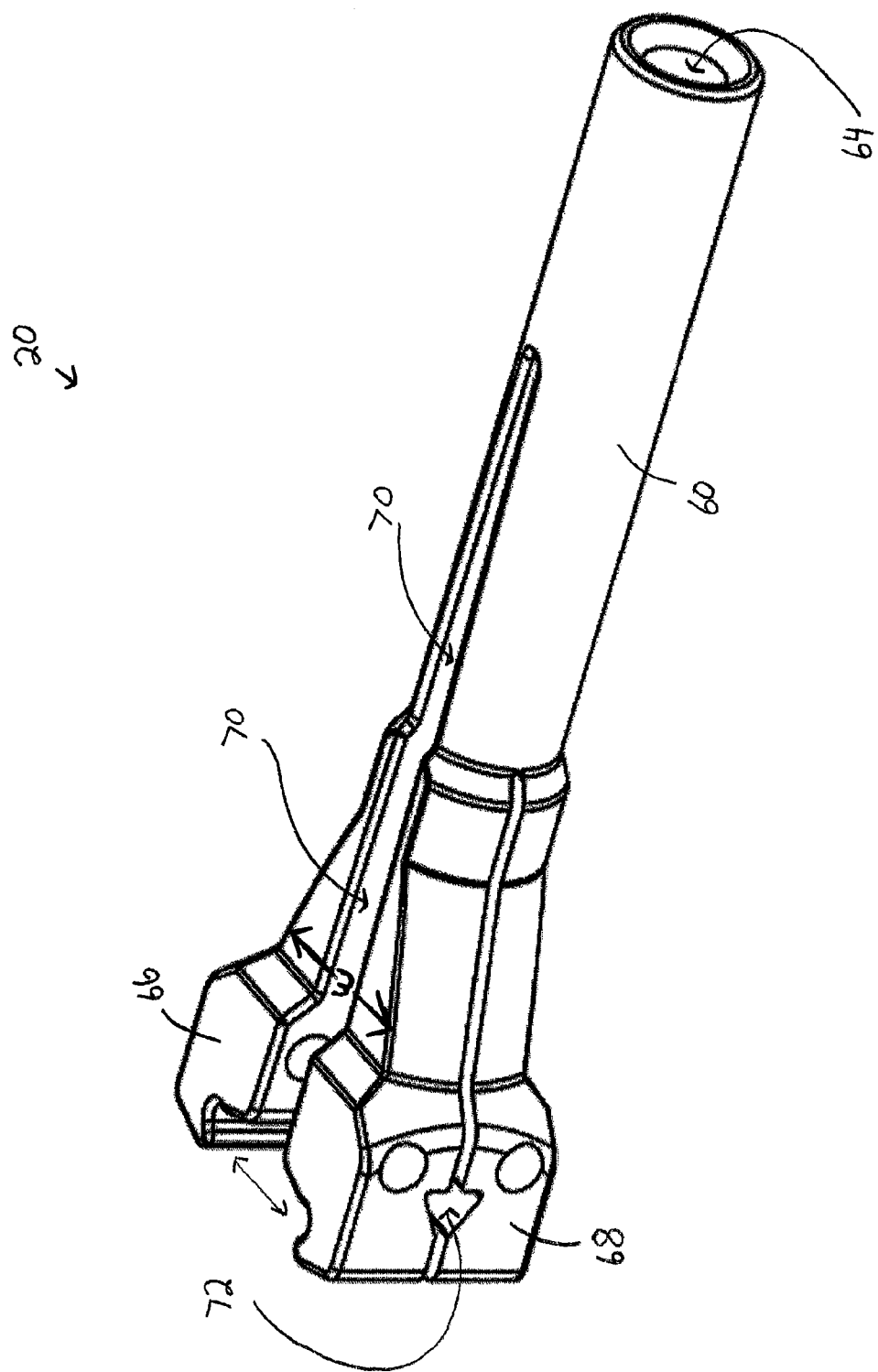
FIG. 5 is a perspective view of an exemplary embodiment of a grasper element.

The device 10 further includes a grasper element 20 adapted to grasp a spinal implant, position the implant within a desired anatomical location (e.g., an intervertebral space), and subsequently release the implant. Again, as will be appreciated by those skilled in the art, a wide variety of such grasping elements 20 can be utilized by the device 10 provided herein. In the exemplary embodiment of FIGS. 4 and 5, the grasper element 20 can include a proximal portion 60 configured to be disposed within a distal opening 62 of the elongate shaft 12 (as indicated by the exploded view of FIG. 4). As shown in FIG. 5, the grasper element 20 includes a first jaw 66 and a second jaw 68 adapted to move (as shown by double-headed arrow in FIG. 5) between a first, open position and a second, closed position wherein the jaws 66, 68 can grasp a spinal implant when in the closed position. Various mechanisms can be utilized to move the jaws 66, 68 between the open and closed positions. In an exemplary embodiment, a connector 74 (as shown in FIG. 3A) extends from an actuator 22 to a proximal portion of the grasper element 20. The distal end 74' of the connector 74 can include a threaded portion adapted to engage a corresponding thread of an inner lumen 64 of the grasper element 20. As a rotational force is applied to the actuator 22, the corresponding threads "pull" the grasper element 20 in a proximal direction so that the grasper element 20 is pulled further into the distal opening 62 of the elongate shaft 12. As the grasper element 20 is pulled into the elongate shaft 12, the walls of the shaft 12 apply a force to the grasper element 20 because the width ("W" in FIG. 5) is greater than the diameter of the distal opening 62. Referring to FIG. 5, a central slit 70 of the grasper element 20 allows for the jaws 66, 68 to move towards one another in response to the force supplied by the walls of the elongate shaft 12. In this embodiment, the jaws 66, 68 can be forced together until they securely grasp an implant. In order to release the implant, the actuator 22 is rotated in a reverse direction such that the grasper is "pushed out" of the distal opening 62 of the elongate shaft 12. As the grasper element 20 moves distally, the force applied by the walls of the shaft 12 dissipates such that the jaws 66, 68 open up (i.e., move away from one another and return to a biased, open position) thereby releasing the implant. As an additional feature, the grasper element 20 can be configured to allow for enhanced visibility by a user so that the implant can be properly positioned within the intervertebral space. For example, the grasper element 20 can include at least one side opening 72 thereby allowing the user to visualize the position of the implant during insertion to the intervertebral space. Various other such features will be apparent to those skilled in the art and are within the spirit and scope of the present invention. Additionally, various other grasper elements and mechanisms for opening/closing the jaws of the grasper element are within the spirit and scope of the present invention such as those disclosed in Assignees' co-pending U.S. patent application Ser. No. 10/750,173, filed on Dec. 31, 2003, entitled "Inserter Instrument and Implant Clip," the entirety of which is hereby incorporated herein by reference.

Figure 6B:
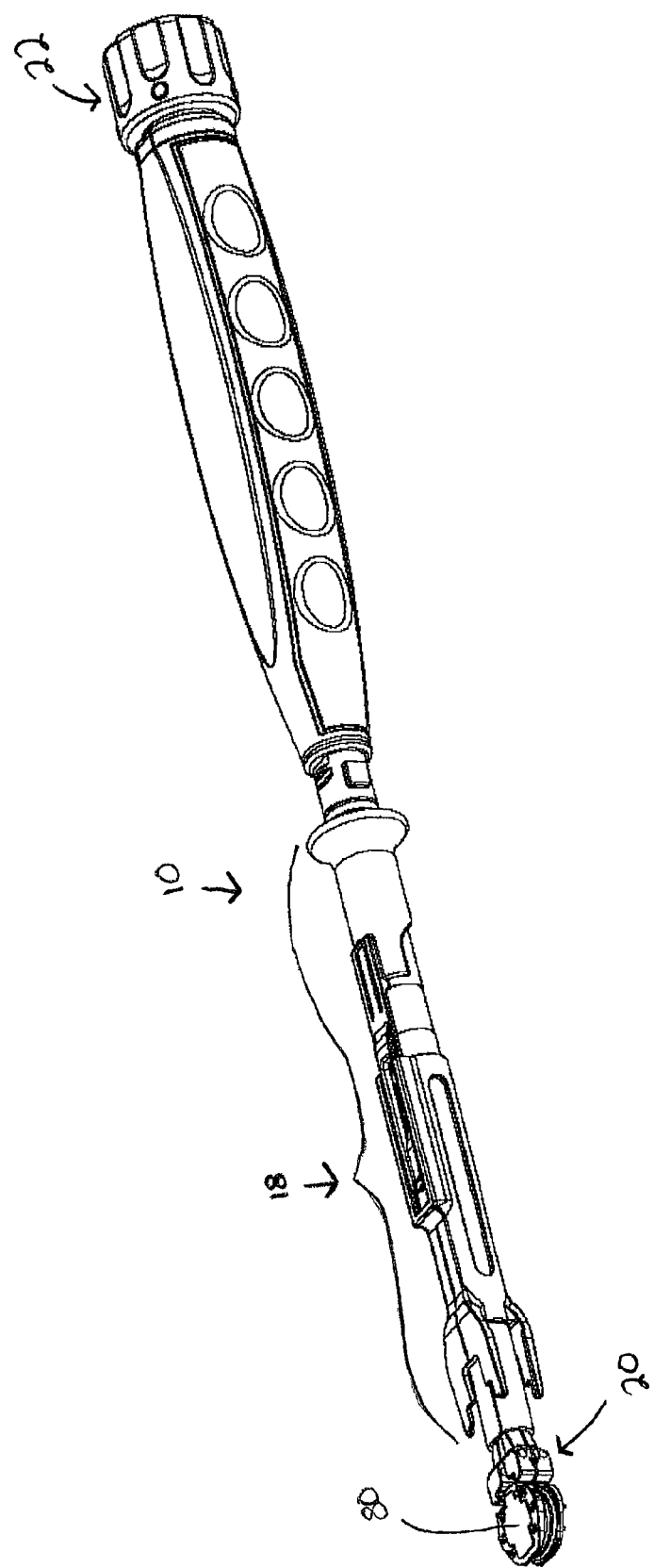
FIG. 6B is a view of the device of FIG. 1 wherein the spinal implant is securely engaged by the grasper element.
Figure 6C:
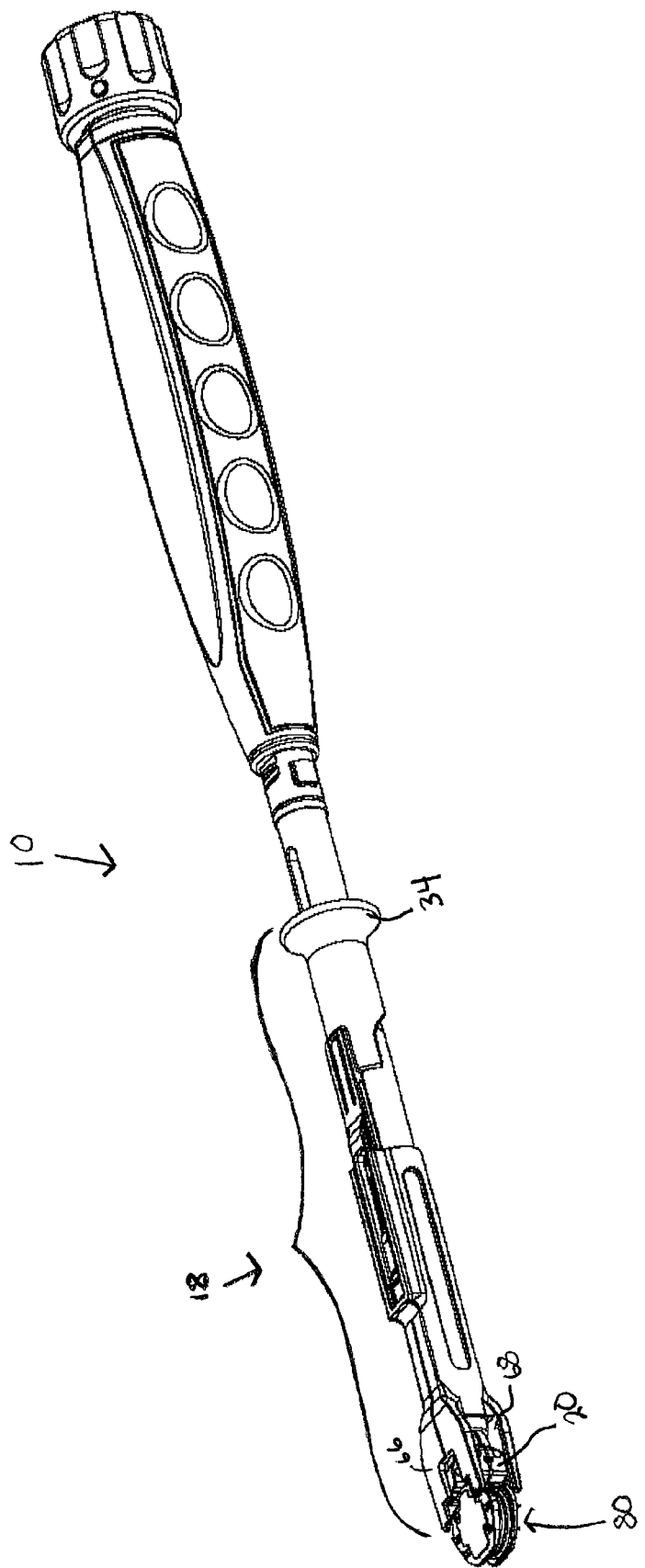
FIG. 6C is a view of the device of FIG. 1 wherein the insertion blade assembly is in the extended position.

FIGS. 6A-6F provide an illustrative example showing a spinal implant 80 being positioned within an intervertebral space. These figures are only meant as an example and in no way limit the spirit and/or scope of the present invention. As shown in FIG. 6A, initially, the insertion blade assembly 18 can be in a retracted position with the jaws of the grasper element 20 in an open position. In this configuration, the device 10 can be utilized to grasp the spinal implant 80 (e.g., an artificial disc.) In FIG. 6B, the jaws of the grasper element 20 have moved from an open position to a closed position by applying a rotational force to the actuator 22. At this stage, the spinal implant 80 is held within the grasping element 20. Next, as shown in FIG. 6C, the insertion blade assembly 18 is slid from a retracted position to an extended position by application of a distal force to the terminal flange 34. As such, in the extended position, at least the distal portion of the insertion blades 66, 68 are adapted to be positioned above and below at least a portion of the superior and inferior surfaces of the implant 80 thereby shielding portions of the implant 80 from respective vertebral endplates of adjacent vertebrae. In this example, the blades 66, 68 shield a set of anterior and central teeth of the implant 80. Once the assembly 18 is in the extended position, the spinal implant 80 can be positioned within the target intervertebral space. As shown in FIG. 6D, the spinal implant is positioned between adjacent vertebrae 82 and 84. During delivery, a portion of the top blade 66 is positioned between the superior surface of the implant 80 and the superior vertebrae 82, and a portion of the bottom blade 68 is positioned between the inferior surface of the implant 80 and the inferior vertebra 84 thereby shielding the implant from respective vertebral endplates of the adjacent vertebra 82, 84.

Figure 6E:
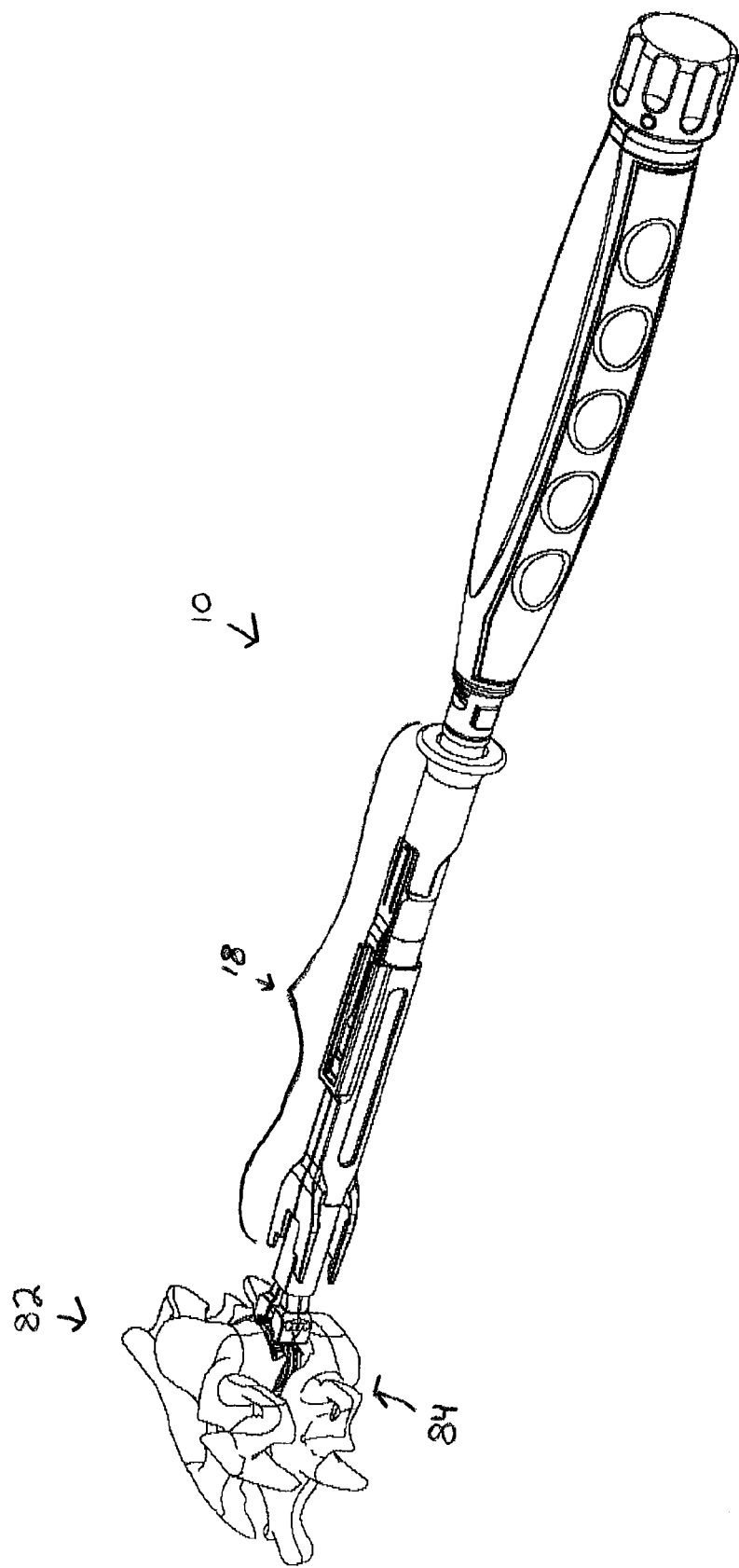
FIG. 6E is a view of the device of FIG. 1 wherein the insertion blade assembly is moved to a retracted position after placement of the implant.
Figure 6F:
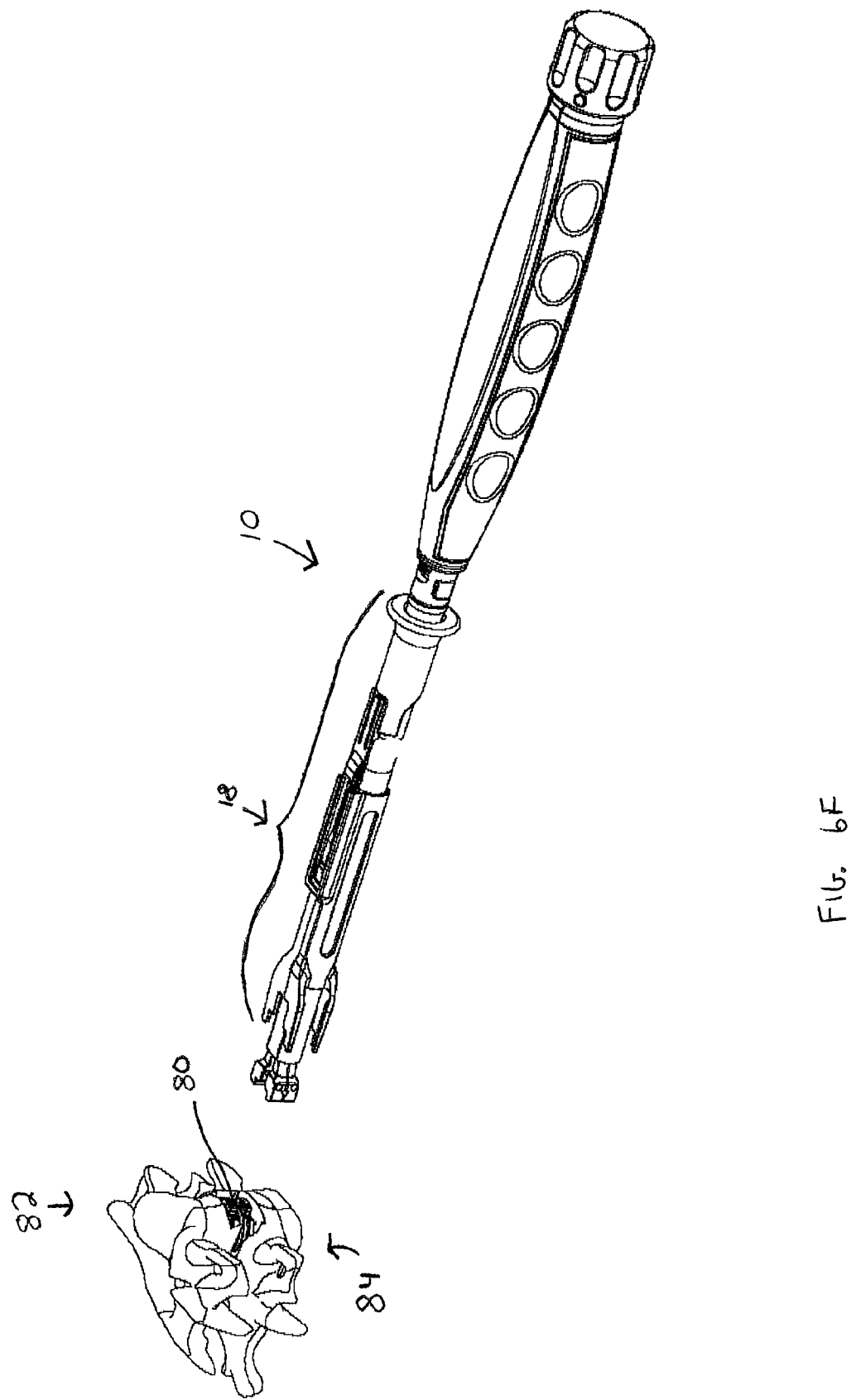
FIG. 6F is a view of the device of FIG. 1 wherein the device is withdrawn from the anatomical location.

As shown in FIG. 6E, once the implant 80 is properly positioned within the intervertebral space, the insertion blade assembly 18 can be slid from the extended position to the retracted position thereby removing any portion of the assembly 18 from the intervertebral space, and allowing the implant 80 (as well as any associated protrusions/teeth) to engage the respective vertebral endplate of adjacent vertebrae 82, 84. Also at this stage, an opposite rotational force (as compared to the initial rotational force) can be applied to the actuator to move the jaws of the grasper element 20 from the closed position to the open position thereby releasing the spinal implant. Once the grasper element 20 releases the implant, as shown in FIG. 6F, the device 10 can be withdrawn from the treatment area.

The various components discussed above (e.g., insertion assembly, blades, handle, elongate shaft, etc.) can be formed from commonly known sterilizable, biocompatible materials. For example, the various components can be formed from any combination of polymers, metals, and metal alloys. Those skilled in the art will appreciate that these are merely examples and any such materials or combination of materials are within the spirit and scope of the present invention.

In addition to the device described above, a method for positioning a spinal implant within an anatomical location is provided. In general, the method allows for portions of an implant to be shielded from respective vertebral endplates of adjacent vertebrae as the implant is positioned within an intervertebral space. More specifically, the method includes grasping a spinal implant with a spinal implant insertion device. Once the implant is held by the device, the method includes sliding a pair of opposed insertion blades along an elongate shaft of the insertion device from a retracted position to an extended position such that in the extended position a top blade is positioned above a portion of the spinal implant and a bottom blade is positioned below a corresponding portion of the spinal implant. Next, the method includes positioning the implant within the desired anatomical location (e.g., an intervertebral space), and sliding the blades from the extended position to the retracted position. Finally, the method includes releasing the spinal implant from the spinal implant insertion device. Additionally, the method can include locking the opposed insertion blades to the elongate shaft of the spinal insertion device when the blades are in a desired position (i.e., the extended position or the retracted position). In an exemplary embodiment, any step of the method can be performed utilizing any of the embodiments of the device described in detail above.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A spinal implant insertion device, comprising:
  an elongate shaft having a proximal end, a distal end, and a central longitudinal axis extending therebetween;
  an insertion blade assembly configured to be slidably mated to an outer portion of the elongate shaft, a distal portion of the insertion blade assembly forming a set of opposed blades, including a first blade positioned above the central longitudinal axis of the elongate shaft and a second blade positioned below the central longitudinal axis of the elongate shaft, the insertion blade assembly being configured to slide relative to the elongate shaft between a retracted position and an extended position; and
  a grasper element formed of first and second jaws, the grasper element being coupled to the distal end of the elongate shaft and being configured to move between a first, open position and a second, closed position that is effective to grasp a spinal implant between the first and second jaws independent of the position of the insertion blade assembly;

wherein the first and second blades of the insertion blade assembly are fixed relative to one another and at least one of the first and second insertion blades includes outer portions that extend distally farther than a central portion of the respective blade;

wherein the elongate shaft includes a first locking mechanism and the insertion blade assembly includes a second locking mechanism, the first and second locking mechanisms being configured to interface to selectively lock the insertion blade assembly at a desired position.

2. The spinal implant insertion device of claim 1, wherein at least one of the first and second blades is substantially planar.

3. The spinal implant insertion device of claim 1, wherein at least one of the first and second blades is substantially U-shaped, having a distal facing opening.

4. The spinal implant insertion device of claim 1, wherein the desired position is the extended position.

5. The spinal implant insertion device of claim 1, wherein a distal end of each of the first and second blades is configured to be positioned proximal to the spinal implant held by the grasper element when the insertion blade assembly is in the retracted position.

6. The spinal implant insertion device of claim 5, wherein the distal end of each of the first and second blades covers at least a portion of an inferior surface and a superior surface of the spinal implant grasped by the grasper element when the assembly is in the extended position.

7. The spinal implant insertion device of claim 1, further comprising an actuator having a connector that extends through an inner lumen of the elongate shaft to engage a proximal portion of the grasper element, the actuator being configured such that a force applied thereto is effective to move the grasper element between the open position and the closed position.

8. The spinal implant insertion device of claim 7, wherein the force is a rotational force.

* * * * *